United States Patent [19]

Jung

[11] Patent Number: 6,132,936
[45] Date of Patent: Oct. 17, 2000

[54] MONOMER AND POLYMER FOR PHOTORESIST, AND PHOTORESIST USING THE SAME

[75] Inventor: Min Ho Jung, Kyoungki-do, Rep. of Korea

[73] Assignee: Hyundai Electronics Industries Co., Ltd., Rep. of Korea

[21] Appl. No.: 09/223,095

[22] Filed: Dec. 30, 1998

[30] Foreign Application Priority Data

Dec. 31, 1997 [KR] Rep. of Korea .................. 97-81391

[51] Int. Cl.$^7$ .................................................. G03F 7/028
[52] U.S. Cl. ................................. 430/281.1; 430/270.1; 526/318; 526/319
[58] Field of Search ............... 430/270.1, 281.1; 526/318, 319

[56] References Cited

U.S. PATENT DOCUMENTS

| | | |
|---|---|---|
| 4,011,386 | 3/1977 | Matsumoto et al. . |
| 4,106,943 | 8/1978 | Ikeda et al. . |
| 4,491,628 | 1/1985 | Ito et al. .................................. 430/176 |

(List continued on next page.)

FOREIGN PATENT DOCUMENTS

| | | |
|---|---|---|
| 0 549 967 A1 | 7/1993 | European Pat. Off. . |
| 794458 | 9/1997 | European Pat. Off. . |
| 0836119A1 | 11/1997 | European Pat. Off. . |
| 01157997 | 6/1989 | Japan . |
| 10232495 | 9/1998 | Japan . |
| 1329997 | 9/1970 | United Kingdom . |
| WO 96/37526 | 11/1996 | WIPO . |
| WO 97/33198 | 9/1997 | WIPO . |

OTHER PUBLICATIONS

CPI–Profile Booklet, 1993, 51087U–AE, No. JA 4805892–Q.
Derwent Abstract No. 26653A/14 of SU 525–709.
Derwent Abstract No. 94–257346/32 of JP 06118399–A.

(List continued on next page.)

*Primary Examiner*—Janet Baxter
*Assistant Examiner*—Yvette M. Clarke
*Attorney, Agent, or Firm*—Townsend and Townsend and Crew LLP

[57] ABSTRACT

The present invention relates to a new monomer of a lithocholylacrylate type, a new photoresist copolymer prepared from the new monomer, a new photoresist composition and processes for preparing same. The photoresist of the present invention may be used in lithography processes using KrF(248 nm) or ArF(193 nm) light sources which are typically used in the manufacture of 1G or 4G DRAM semi-conductor integrated circuits. The new monomer of the present invention is represented by following Formula II:

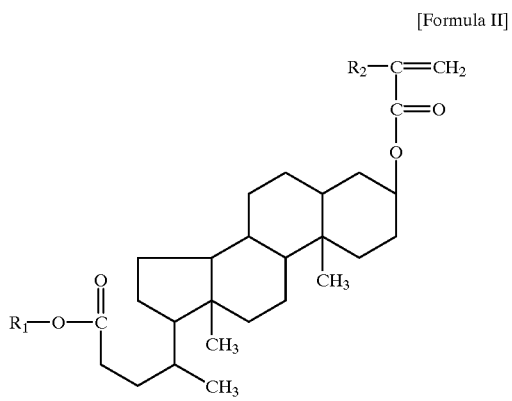

[Formula II]

wherein, $R_1$ represents hydrogen, a substituted or non-substituted $C_1$–$C_{10}$ straight or branched chain alkyl group, a cycloalkyl group, an alkoxyalkyl group, or a cycloalkoxyalkyl group; and $R_2$ represents hydrogen or a methyl group. A representative new photoresist copolymer of the present invention is represented by the following Formula VII:

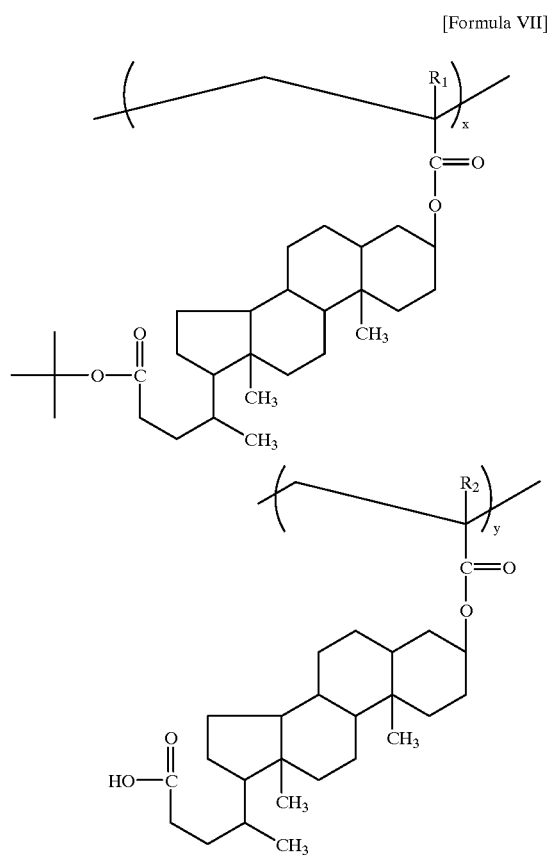

[Formula VII]

wherein, $R_1$ and $R_2$ independently represent hydrogen or a methyl group, and x and y independently represent a mole fraction between 0.05 and 0.9.

14 Claims, No Drawings

U.S. PATENT DOCUMENTS

| | | | |
|---|---|---|---|
| 4,637,896 | 1/1987 | Shannon | 252/299.7 |
| 4,883,740 | 11/1989 | Schwalm et al. | 430/270 |
| 5,087,677 | 2/1992 | Brekner et al. | 526/160 |
| 5,158,855 | 10/1992 | Sugiyama et al. | 430/192 |
| 5,212,043 | 5/1993 | Yamamoto et al. | 430/192 |
| 5,252,427 | 10/1993 | Bauer et al. | 430/270 |
| 5,278,214 | 1/1994 | Moriya et al. | |
| 5,580,694 | 12/1996 | Allen et al. | 430/270.1 |
| 5,786,131 | 7/1998 | Allen et al. | 430/270.1 |

OTHER PUBLICATIONS

Thomas I. Wallow, et al., "Evaluation of Cycloolefin–Maleic Anhydride Alternating Copolymers as Single–Layer Photoresist for 193nm Photolithography", 1996, Proc. SPIE, vol. 2724, 355–364.

R.D. Allen et al., "The Influence of Photoacid Structure on the Design and Performance of 193nm Resists", 1997, Journal of Photopolymer Science and Technology, vol. 10, 503–510.

F.M. Houlihan et al., "A Commercially Viable 193nm single Layer Resist Platform", 1997, Journal of Photopolymer Science and Technology, vol. 10, 511–520.

J.C. Jung et al., "ArF Single Layer Resist Composed of Alicyclic Main Chain Containing Maleic Anhydride", 1997, Journal of Photopolymer Science and Technology, vol. 10, 592–533.

S. J. Choi et al., "New ArF Single–layer Resist for 193–nm Lithography", 1997, Journal of Photopolymer Science and Technology, vol. 10, 521–528.

T. Hattori et al., "Synthesis and Dissolution Characteristics of Novel Alicyclic Polymer With Monoacid Ester Structures" 1997, Journal of Photopolymer Science and Technology, vol. 10, 535–544.

K. Nozaki and Ei Yaro, "New Protective Groups in Methacrylate Polymer for 193–nm Resists", 1997, Journal of Photopolymer Science and Technology, vol. 10, 545–550.

K. Nakano et al., "Chemically Amplified Resist Based on High Etch–Resistant Polymer for 193–nm Lithography", 1997, Journal of Photopolymer Science and Technology, vol. 10, 561–569.

CA Register No. 100207–98–5.

CA Register No. 32759–57–2.

CA Register No. 27056–70–8.

CA Register No. 174659–58–6.

CA Register No. 28503–41–5.

CA Register No. 194997–59–6.

CA Abstract No. 104:149512 & Macromolecules 19(4) 1266–8 (1986).

CA Abstract No. 91:124064 & Makromol. Chem. 180(8) 1975–88 (1979).

CA Abstract No. 113:24734 & JP 02 051511.

CA Abstract No. 127:227269 & J Photopolym. Sci. Technol. 10(4) 529–534 (1997).

CA Abstract No. 124:317926 & Marcomol. Rapid Commun. 17(3) 173–180 (1996).

CA Abstract No. 124:203171 & Macromolecules 29(8) 2755–63 (1996).

CA Abstract No. 127:227308 & Proc. SPIE–Int. Soc. Opt. Eng. (1997) 3049 Advances in Resist Technology and Processing XIV 92–103.

CA Abstract No. 66:18889 & Magy. Kem. Foly. (1966) 72(11)491–3.

CA Abstract No. 199328–07–9.

MONOMER AND POLYMER FOR PHOTORESIST, AND PHOTORESIST USING THE SAME

BACKGROUND OF THE INVENTION

1. Field of the Invention

The present invention relates to a new monomer and polymer used in making a photoresist, and a photoresist composition comprising the same. More specifically, it relates to a new monomer of a lithocholylacrylate type and introducing the new monomer to a polymer to form a photoresist. The photoresist preferably is used in a lithography process using a KrF(248 nm) or an ArF(193 nm) light source, which are light sources that can be used in the manufacture of 1G or 4G Dynamic Random Access Memory ("DRAM") semi-conductor integrated circuits.

2. Description of the Prior Art

In general, a photoresist resin which is to be used with an ArF source should have suitable etching resistance and adhesiveness, with low light absorption at 193 nm wavelength. Such a photoresist resin typically is developable by using about 2.38 wt % aqueous tetramethylammonium hydroxide(TMAH) solution. However, these types of photoresist resins are difficult to synthesize. Up to now, many researchers have focused their studies on novolac type resins to increase transparency at 193 nm wavelength and increase etching resistance. As a part of this research, a three component resist system has been suggested by Bell laboratory. The resist system suggested by Bell Labs uses a lithocholic ester compound as a dissolution inhibitor and a copolymer resin represented by the following Formula I, wherein the copolymer resin has, norbornene acrylate and maleic anhydride substituents in the main chain:

[Formula I]

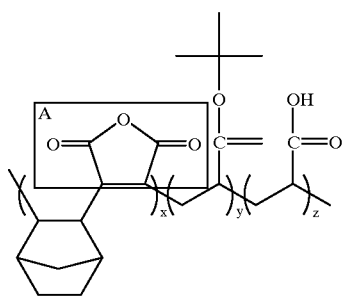

The lithocholic ester compound used in the aforementioned resist system has excellent etching resistance and high transparency at far-ultraviolet rays, particularly at 193 nm. However, when too much of the lithocholic ester compound is included in the resist composition, for example 40 wt % or more, a residue is extracted by crystallization.

As one skilled in the art will appreciate, flow of the resist typically occurs during a heat-treating process such as pre-bake process or post-bake process, which lowers the free transition temperature(Tg) of the lithocholic ester compound; for example to about 100° C. and below. Thus, if the resist contains a residue from the lithocholic ester compound, the photoresist pattern may be distorted, thereby adversely affecting the resolution of the etching process.

SUMMARY OF THE INVENTION

The present invention relates to a new monomer and polymer used in making a photoresist, and a photoresist composition comprising the same. Preferably, a new monomer of a lithocholylacrylate type is prepared and introduced into a polymer to form a photoresist. The photoresist preferably is used in a lithography process using a KrF(248 nm) or an ArF(193 nm) light source, which are light sources typically used in the manufacture of 1G or 4G DRAM circuits. As a result, the photoresist of the present invention has high free transition temperature(Tg), which makes the photoresist chemically modifiable, has low absorption at the far ultraviolet region of the spectrum, particularly at 193 nm, and has excellent etching resistance. The photoresist composition preferably is formed by introducing a polycyclic unit into a side chain, which can be easily accomplished by conventional radical polymerization and easily separated using a protective group.

Accordingly, it is an object of the present invention to provide a new monomer of the lithocholylacidyl(meth)acrylate type.

It is another object of the present invention to provide a new photoresist polymer from the new monomer.

Other objects of the present invention are to provide a photoresist composition comprising the polymer, and a semiconductor device manufactured by using the photoresist composition.

DETAILED DESCRIPTION OF THE INVENTION

In accordance with one aspect of the present invention, a monomer represented by the following Formula II is provided,

[Formula II]

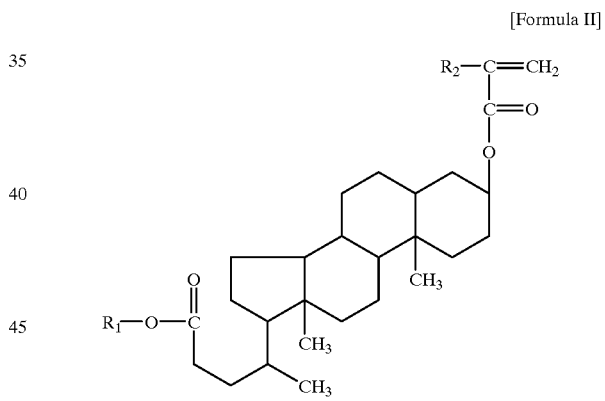

wherein, $R_1$ represents hydrogen, a substituted or non-substituted $C_1$–$C_{10}$ straight or branched chain alkyl group, a cycloalkyl group, an alkoxyalkyl group, or a cycloalkoxyalkyl group; and $R_2$ represents hydrogen or a methyl group.

In accordance with another aspect of the present invention, a copolymer photoresist formed by the polymerization of the monomer of the Formula II is provided.

In accordance with still another aspect of the present invention, a photoresist composition comprising the copolymer according the present invention, an organic solvent, and a photoacid generator is provided.

PREPARATION OF NEW MONOMER

In accordance with one embodiment of the present invention, lithocholic acid is bonded with (meth)acrylic acid to form a monomer represented by the following Formula II:

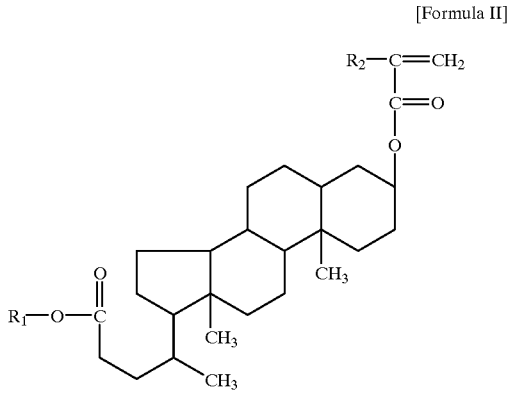

[Formula II]

wherein $R_1$ is hydrogen, a substituted or non-substituted $C_1$–$C_{10}$ straight or branched chain alkyl group, a cycloalkyl group, an alkoxyalkyl group, or a cycloalkoxyalkyl group; and $R_2$ is hydrogen or methyl group.

In accordance with this aspect of the present invention, by introducing the above monomer in the polymer structure, the photoresist of the present invention has a high free transition temperature(Tg), which makes the photoresist chemically modifiable has low absorption of light in the far ultra-violet region, particularly at 193 nm, and has excellent etching resistance.

The following examples illustrate the synthesis of the monomers of the present invention, but are not intended to limit the invention thereto:

EXAMPLE I

Synthesis of 5β-cholan-24-oic acidyl-3-(meth)acrylate monomer

In a round 250 ml flask, 5β-cholan-24-oic acid (37.7 g) is dissolved in 100 ml of tetrahydrofuran solvent. To the mixture, trimethylamine (11.2 g) is added and stirred homogeneously at a temperature of 0° C. Then, (meth)acryloylchloride (10.5 g) is added thereto and the reaction is carried out for 5 hours. When the reaction is completed, the resultant product is separated and dried by using column chromatography to obtain 32 g (yield: 72%) of the monomer represented by the following Formula III:

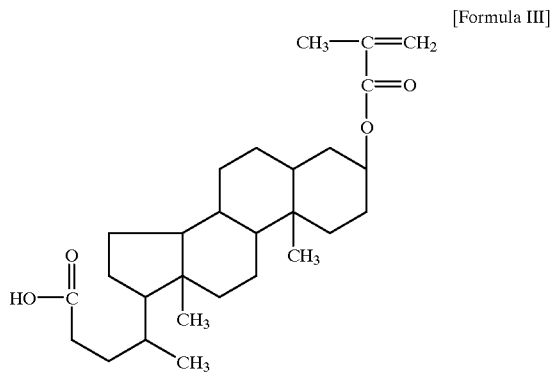

[Formula III]

EXAMPLE II

Synthesis of 5β-(t-butoxycarbonyl)-cholan-24-yl-3-(meth)acrylate

In a round 250 ml flask, 5β-cholan-24-oic acidyl-3-(meth)acrylate (15 g) prepared according to Example I is dissolved in 100 ml of tetrahydrofuran solvent, and thionylchloride (4.8 g) is added to the mixture. Tert-butanol (4.9 g) is added to the reaction solution dropwise with a funnel, the reaction is performed at a temperature of 0° C. for 2 hours, and then at ambient temperature for 5 hours. When the reaction is completed, the resultant product is separated and dried using column chromatography to obtain 12.6 g (yield: 75%) of the monomer represented by the following Formula IV:

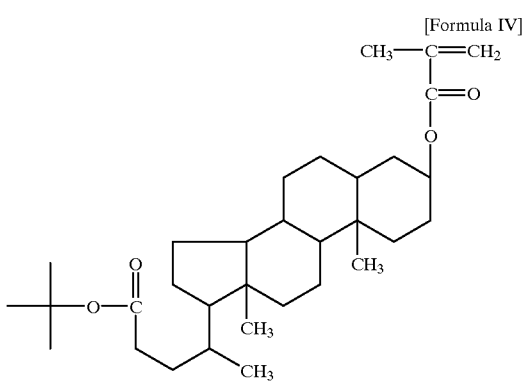

[Formula IV]

EXAMPLE III

Synthesis of 5β-(hydropyranyl)-cholan-24-yl-3-(meth)acrylate

In a 250 ml round flask, 5β-cholan-24-oic acidyl-3-(meth)acrylate (15 g) prepared according to Example I is dissolved in 100 ml tetrahydrofuran solvent, and p-toluenesulfonic acid (0.3 g) is added to the mixture. 3,4-dihydro-2H-pyran (5.6 g) is added to the reaction solution, dropwise with a funnel, and the reaction is performed at a temperature of 0° C. for 8 hours. When the reaction is completed, the resultant product is separated and dried by using column chromatography to obtain 13.8 g(yield: 78%) of the monomer represented by the following Formula V:

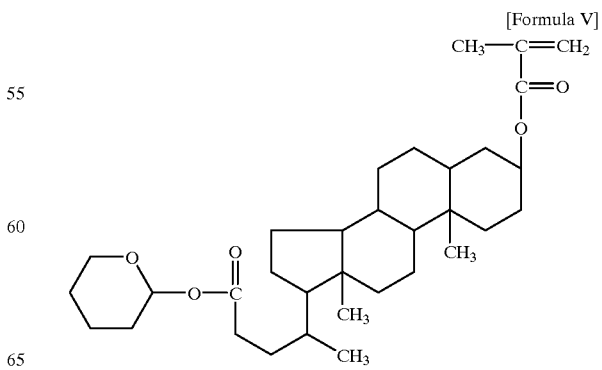

[Formula V]

EXAMPLE IV

Synthesis of 5β-(2-ethoxyethyl)-cholan-24-yl-3-(meth)acrylate

In a round 250 ml flask, 5β-cholan-24-oic acidyl-3-(meth)acrylate (15 g) prepared according to Example I is dissolved in tetrahydrofuran solvent, and p-toluenesulfonic acid (0.3 g) is added to the mixture. Ethyl vinyl ether (4.8 g) is added to the reaction solution dropwise with a funnel and the reaction is performed at a temperature of 0° C. for 8 hours. When the reaction is completed, the resultant product is separated and dried using column chromatography to obtain 13.1 g (yield: 75%) of the monomer represented by the following Formula VI:

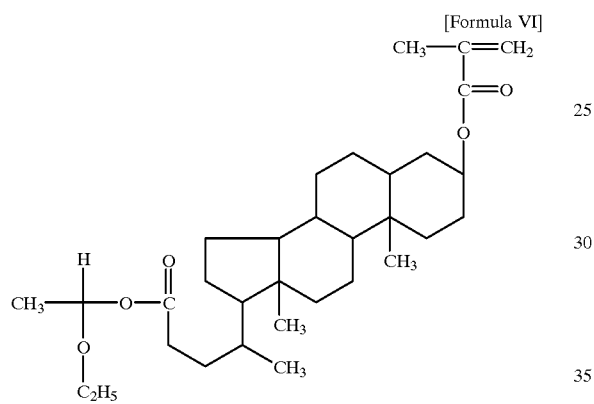

[Formula VI]

Copolymer Resin and Preparation of the same

The copolymers according to the present invention are formed using the lithocholylacidyl(meth)acrylates monomers represented by the Formula II, and are preferably selected from the group consisting of copolymers represented by the following Formulas VII to X:

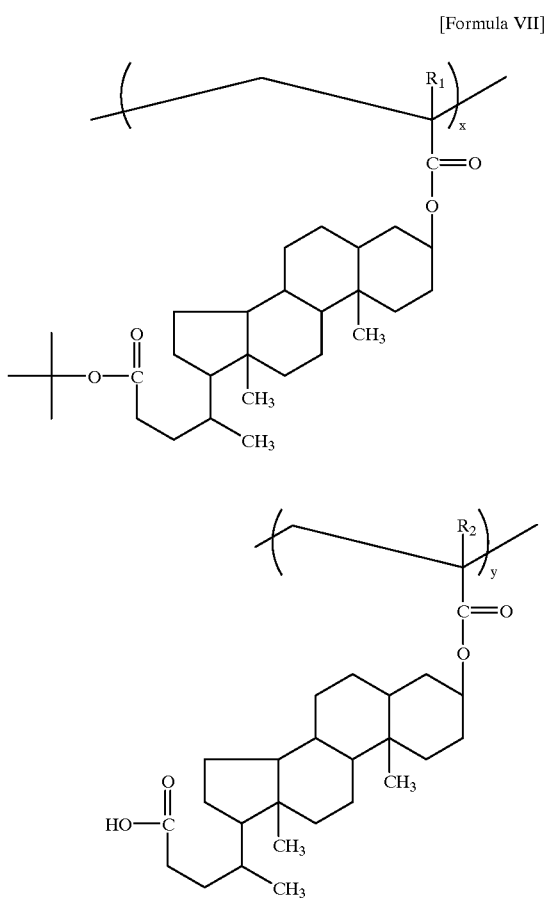

[Formula VII]

wherein, $R_1$ and $R_2$ independently represent hydrogen or a methyl group, and x and y independently represent a mole fraction between 0.05 and 0.9;

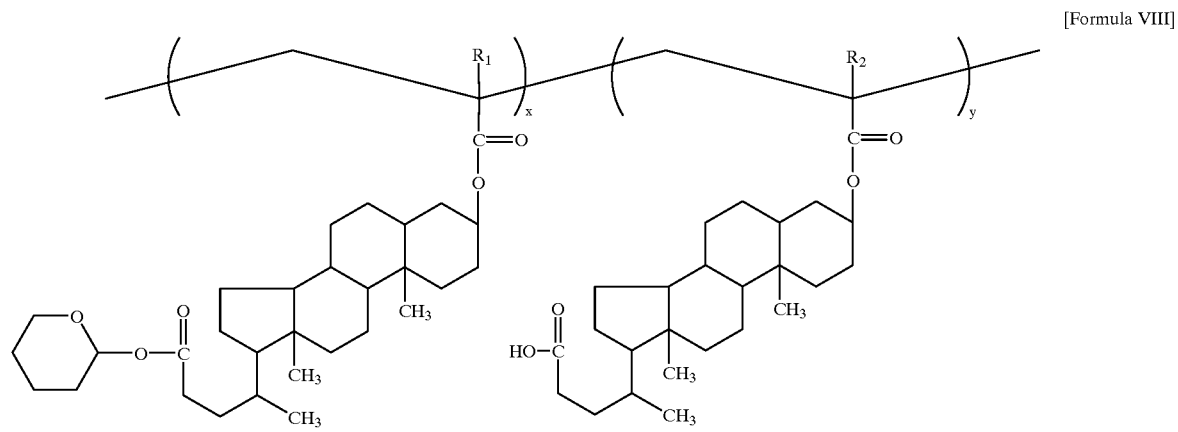

[Formula VIII]

wherein, $R_1$ and $R_2$ independently represent hydrogen or a methyl group, and x and y independently represent a mole fraction between 0.05 and 0.9;

[Formula IX]

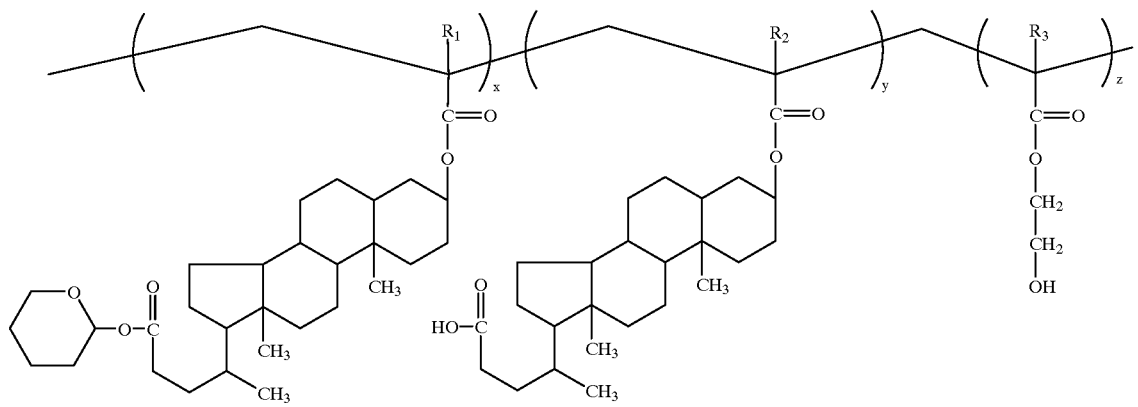

wherein, $R_1$, $R_2$ and $R_3$ independently represent hydrogen or a methyl group, x represents mole fraction between 0.005 to 0.9, and y and z independently represent a mole fraction between 0.001 and 0.9; and

[Formula X]

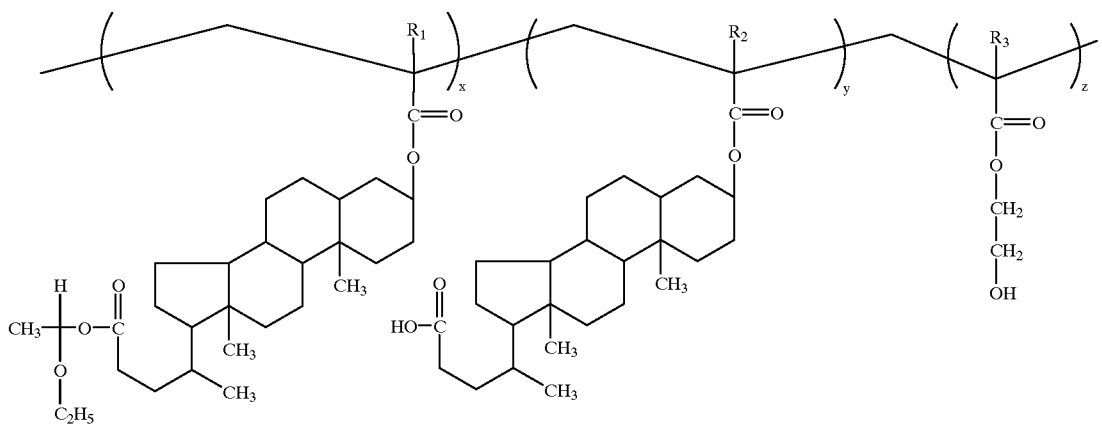

wherein, $R_1$, $R_2$ and $R_3$ independently represent hydrogen or a methyl group, x represents mole fraction between 0.005 to 0.9, and y and z independently represent a mole fraction between 0.001 and 0.9.

Preparation Process for the Copolymer

The process for preparing the copolymer preferably comprises the steps of dissolving a first and second monomer represented by Formula II, which may be the same or different, and then polymerizing the monomers by adding a polymerization initiator to the resultant solution.

Alternatively, a (meth)-acrylate compound substituted by an hydroxyalkyl group may be used as a third monomer in the polymerization process. This third monomer is preferably a compound represented by the following Formula XV:

[Formula XV]

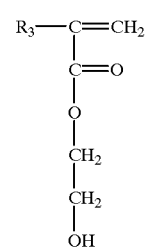

wherein $R_3$ represents hydrogen or a methyl group.

A copolymer resin of Formula VII can be prepared by polymerizing 5β-buthoxycarbonyl)-cholan-24-yl-3-(meth) acrylate with 5β-cholan-24-oic acidyl-3-(meth)acrylate in the presence of a radical initiator, as illustrated in the following reaction scheme I:

[Scheme I]

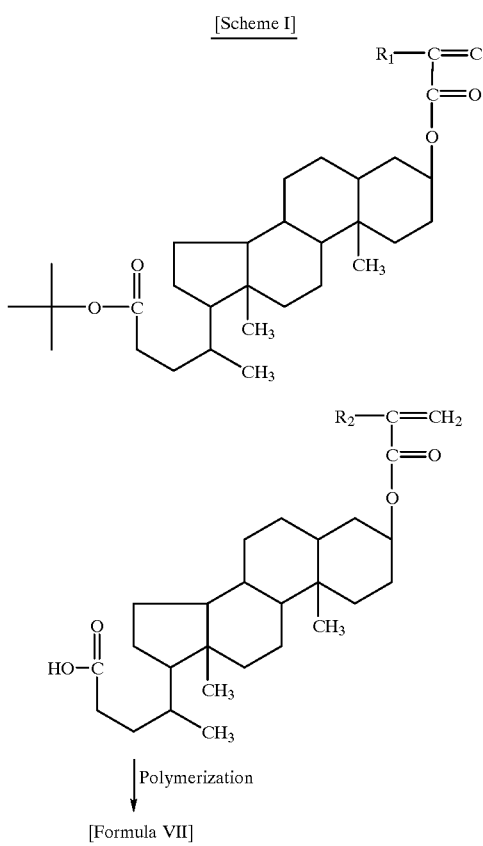

[Formula VII]

A copolymer resin of the Formula VIII can be prepared by polymerizing 5β-(hydropyranyl)-cholan-24-yl-3-(meth)acrylate with 5β-cholan-24-oic acidyl-3-(meth)acrylate in the presence of a radical initiator, as illustrated in the following reaction scheme II:

[Scheme II]

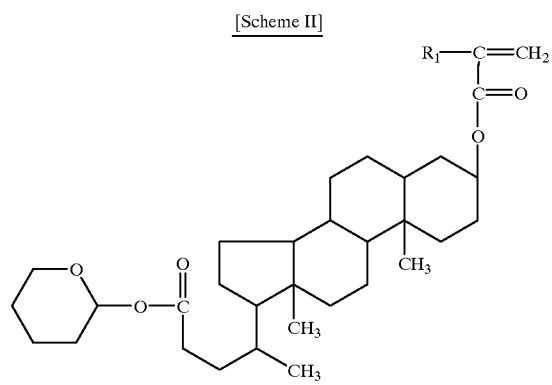

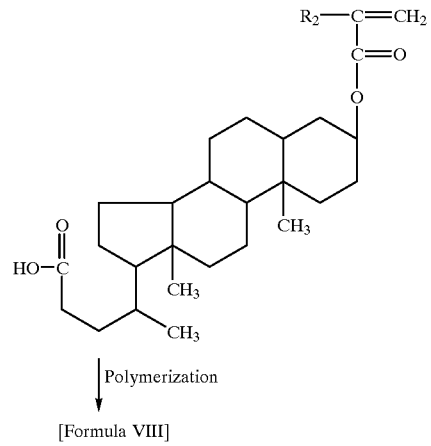

[Formula VIII]

A copolymer resin of the Formula IX can be prepared by polymerizing 5β-(hydropyranyl)-cholan-24-yl-3-(meth)acrylate, 5β-cholan-24-oic acidyl-3-(meth)acrylate and 2-hydroxyethyl (meth)acrylate in the presence of a radical initiator, as illustrated in the following reaction scheme III:

[Scheme III]

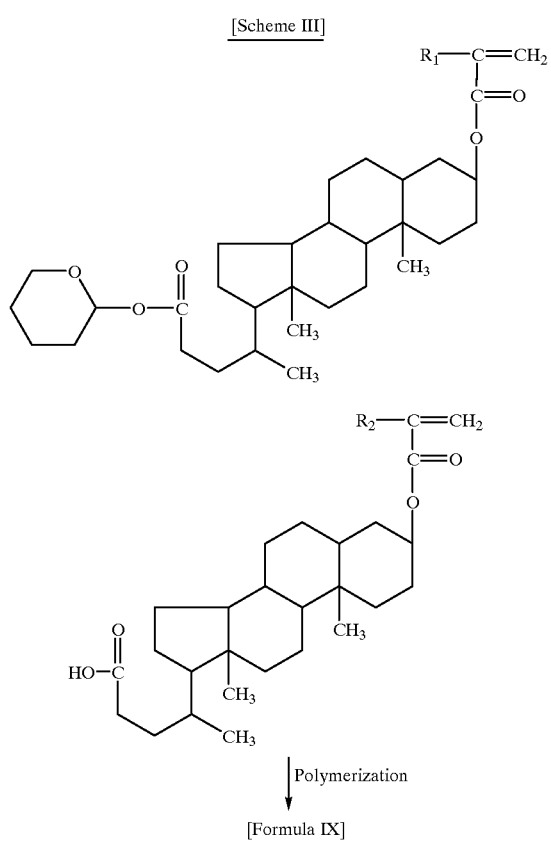

[Formula IX]

-continued

R₃—C=CH₂
|
C=O
|
O
|
CH₂
|
CH₂
|
OH

A copolymer resin of the Formula X can be prepared by polymerizing 5β-(2-ethoxyethyl)-cholan-24-yl-3-(meth)acrylate, 5β-cholan-24-oic acidyl-3-(meth)acrylate and 2-hydroxyethyl (meth)acrylate in the presence of a radical initiator, as illustrated in the following reaction scheme IV:

[Scheme IV]

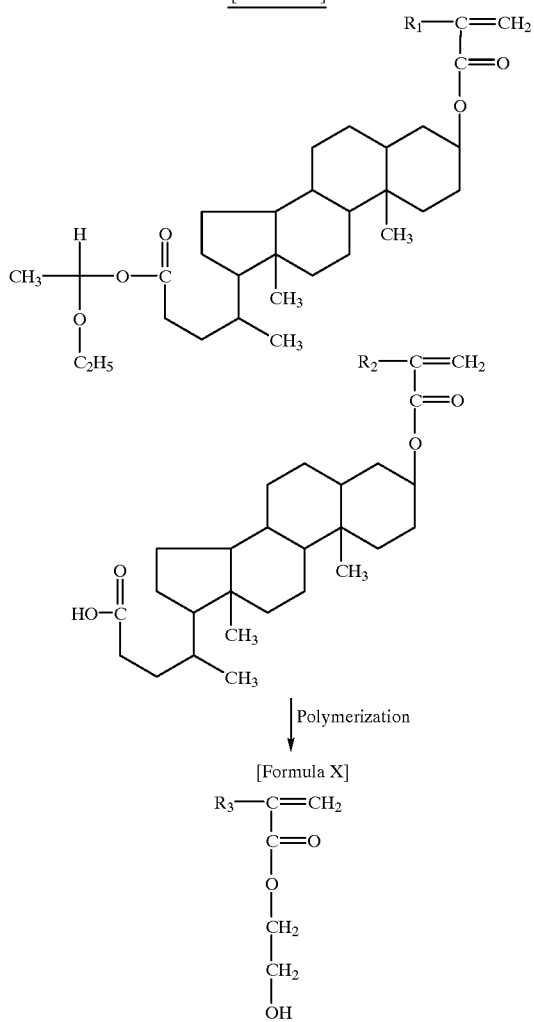

The aforementioned copolymer resins (Formulas VII to X) are prepared according to the present invention by a conventional polymerization process such as bulk polymerization or solution polymerization. Polymerization organic solvents which may be used in the present invention include methyl 3-methoxypropionate, ethyl 3-ethoxypropionate, propylene glycol methyl ether acetate, cyclohexanone, and the like.

In the process for preparing the copolymer resin according to the present invention, general polymerization conditions, including temperature and pressure of radical polymerization, may vary depending upon the property of the reactants used, but it is preferable to carry out the polymerization reaction at a temperature between about 60° C. and about 200° C. under a pressure between about 50 and about 200 atm.

The copolymer resin according to the present invention can be prepared by copolymerizing a lithocholicacidyl (meth)acrylate monomer having a hydrophilic group (molecular weight: 3,000–100,000). The copolymer resin prepared according to the present invention can be advantageously used in lithography processes using a KrF(248 nm) or ArF(193 nm) light source, which is typically used in the manufacture of 1G and/or 4G DRAM integrated circuit semi-conductors.

Synthesis of Photoresist Composition

The copolymer resin photoresist composition according to the present invention can be prepared using a conventional process for forming a photoresist composition; that is, by mixing the photoresist resin with a conventional photo-acid generator in the presence of an organic solvent to form a photoresist solution. This photoresist composition can be used to form a positive micro-image. Preferably, the copolymer resin of the present invention is dissolved in cyclohexanone at a concentration of about 10% to about 30% by weight. An inorganic acid generator is mixed with the copolymer resin at a concentration of about 0.1% to about 10% by weight. The mixture is then filtered with an ultra-micro filter to provide the photoresist solution. Preferred photoacid generators used in this process include triphenylsulfonium triflate, dibutylnaphthylsulfonium triflate, 2,6-dimethylphenylsulfonate, bis(arylsulfonyl)-diazomethane, oximsulfonate, 2,1-diazonaphthoquinon-4-sulfonate, and the like. After the photoresist solution is formed, it preferably is spin-coated on a silicon wafer to form a thin film thereon. The wafer with the thin film then is soft-baked in an oven or on a heating plate at about 70° C. to about 200° C., and more preferably at about 80° C. to about 150° C., for about 1 to 5 minutes. After heating, the photoresist film is exposed to light by using an exposer, and then post-baked at about 70° C. to about 200° C., and more preferably at about 100° C. to about 200° C., for about 10 seconds to about 60 minutes. The exposed wafer is impregnated with a 2.38 wt % aqueous TMAH solution for about 1 to about 30 seconds to obtain a ultra-micro photoresist pattern. The light source used to expose the photoresist may be ArF, KrF, E-beam, X-ray, EUV, DUV, or ion-beam.

Other suitable photoacid generators include salts such as diphenyliodine hexafluorophosphate, diphenyliodine hexafluoroarsenate, diphenyliodine hexafluoro antimonate, diphenyl p-methoxyphenyl triflate, diphenyl p-toluenyl triflate, triphenylsulonium hexafluorophosphate, triphenylsulfonium hexafluoroarsenate, triphenlsulfonium hexafluoroantimonate, and the like, or onium salts may be used.

A better understanding of the present invention may be obtained in light of following examples which are set forth to illustrate, but are not to be construed to limit, the present invention.

EXAMPLE V

Synthesis of poly[5β-(t-butoxycarbonyl)-cholan-24-yl-3-(meth)acrylate/5β-cholan-24-oic acidyl-3-(meth)acrylate] copolymer (Formula XI)

5β-(t-butoxycarbonyl)-cholan-24-yl-3-(meth)acrylate (0.05 mole) and 5β-cholan-24-oic acidyl-3-(meth)acrylate (0.05 mole) are dissolved in TFT solvent. Then, azobisisobutyronitrite (AIBN) (0.02 g) is added thereto as a polymerization initiator, and the reaction is performed at a temperature of about 70° C. under nitrogen atmosphere for about 15 hours. Crude product thus obtained is precipitated from ethyl ether, and the precipitate is dried to give 32.4 g(yield: 80%, Tg: 138° C.) of the copolymer (molecular weight: 10500) represented by the following Formula XI:

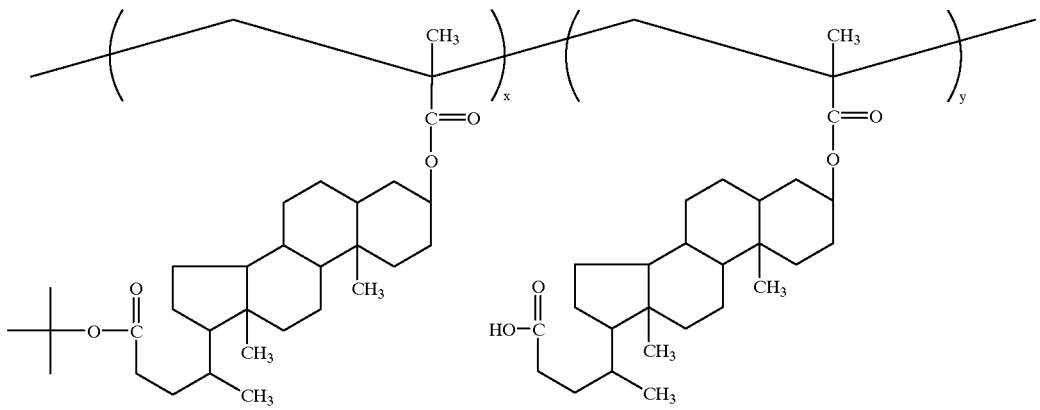

[Formula XI]

The copolymer resin prepared has low absorption at 193 nm, increased etching resistance, and high sensitivity and resolution (sensitivity: 18 mJ/cm2).

EXAMPLE VI

Synthesis of poly[5β-(hydropyranyl)-cholan-24-yl-3-(meth)acrylate/5β-cholan-24-oic acidyl-3-(meth)acrylate] copolymer (Formula XII)

5β-(hydropyranyl)-cholan-24-yl-3-(meth)acrylate (0.04 mole) and 5β-cholan-24-oic acidyl-3-(meth)acrylate (0.04 mole) are dissolved in TFT solvent. Then, AIBN (0.012 g) is added thereto as a polymerization initiator and the reaction is performed at a temperature of about 67° C. under argon atmosphere for about 20 hours. Crude product thus obtained is precipitated from hexane, and the precipitate is dried to give 40.4 g (yield: 84%, Tg: 136° C.) of the copolymer (molecular weight: 9800) represented by the following Formula XII:

The copolymer resin prepared is an excellent photoresist having increased sensitivity without deteriorating etching resistance (sensitivity: 14 mJ/cm$^2$).

EXAMPLE VII

Synthesis of poly[5β-(hydropyranyl)-cholan-24-yl-3-(meth)acrylate/5β-cholan-24-oic acidyl-3-(meth)acrylate/2-hydroxyethyl(meth)acrylate] copolymer (Formula XIII)

5β-(hydropyranyl)-cholan-24-yl-3-(meth)acrylate (0.05 mole), 5β-cholan-24-oic acidyl-3-(meth)acrylate (0.05 mole), and 2-hydroxyethyl(meth)acrylate (0.01 mole) are dissolved in TFT solvent. Then, AIBN (0.018 g) is added thereto as a polymerization initiator and the reaction is performed at a temperature of about 70° C. under nitrogen atmosphere for about 15 hours. Crude product thus obtained is precipitated from ethyl ether, and the precipitate is dried to give 41.7 g (yield: 83%, Tg: 131° C.) of the copolymer (molecular weight: 12500) represented by the following Formula XIII:

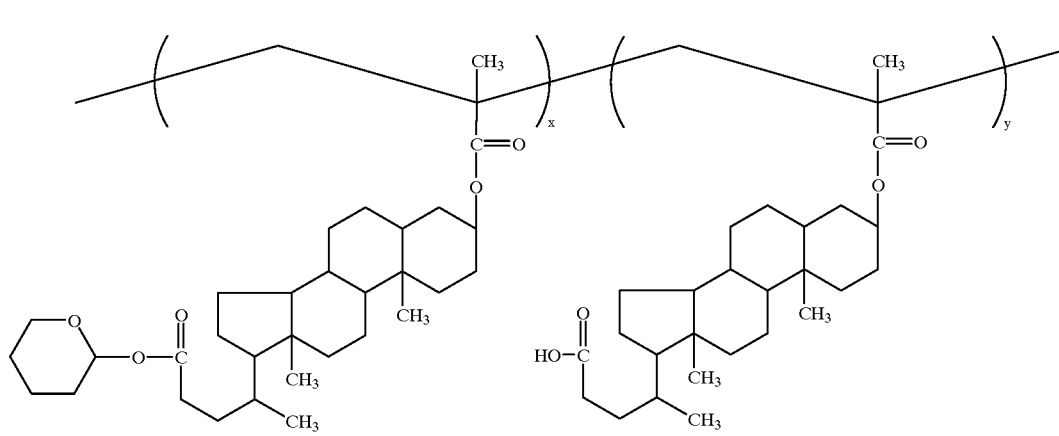

[Formula XII]

[Formula XIII]

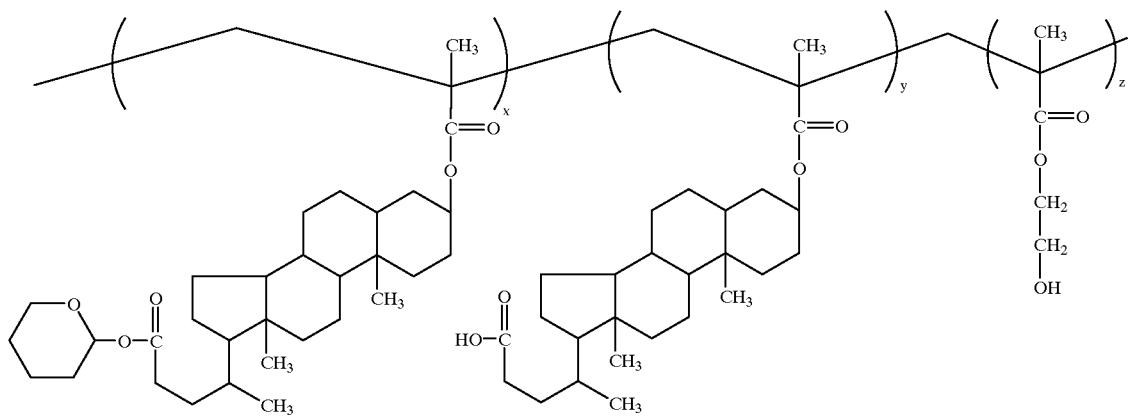

The copolymer resin prepared has similar properties to the copolymer resin obtained in Example V.

EXAMPLE VIII

Synthesis of poly[5β-(2-ethoxyethyl)-cholan-24-yl-3-(meth)acrylate/5β-cholan-24-oic acidyl-3-(meth)acrylate/2-hydroxyethyl(meth)acrylate] copolymer (Formula XIV)

5β-(2-ethoxyethyl)-cholan-24-yl-3-(meth)acrylate (0.05 mole), 5β-cholan-24-oic acidyl-3-(meth)acrylate (0.05 mole), and 2-hydroxyethyl(meth)acrylate (0.01 mole) are dissolved in TFT solvent. Then, AIBN (0.017 g) is added thereto as a polymerization initiator and the reaction is performed at a temperature of about 65° C. under argon atmosphere for about 15 hours. Crude product thus obtained is precipitated from ethyl ether, and the precipitate is dried to give 48.7 g(yield: 84%, Tg: 128° C.) of the copolymer (molecular weight: 11500) represented by the following Formula XIV:

The copolymer resin prepared is an excellent photoresist, particularly with regard to contrast.

EXAMPLE IX

Formation of Photoresist Pattern

The copolymer resin (Formula XI) (10 g) created by the process of Example V is dissolved in 3-methoxymethylpropionate (40 g) solvent, and triphenyl sulfonium triflate (0.211 g) is added and stirred. Thereafter, the mixture is filtered through a 0.10 μm filter to give a photoresist solution. Then, the photoresist solution is spin-coated on the surface of a wafer forming a thin film having the thickness of about 0.4 μm. The wafer then is soft-baked in an oven of about 100° C. for about 4 minutes. Next, the photoresist is exposed to light having a wavelength of about of 250 nm, by using an exposer, and then the wafer is post-baked at about 120° C. Finally, the exposed wafer is impregnated in with aqueous TMAH solution having a concentration of about 0.01% by weight as a developing solution, for about 1.5 minutes to obtain ultra-micro photoresist pattern(resolution: 0.15 μm, sensitivity: 18 mJ/cm2).

[Formula XIV]

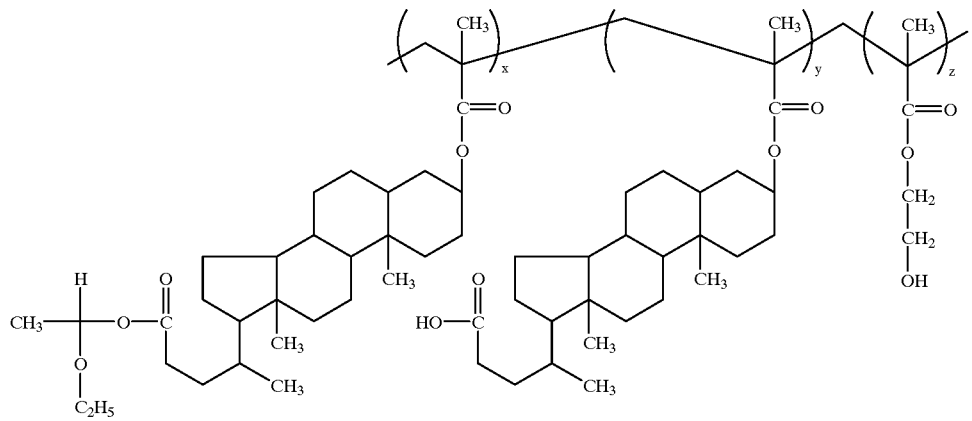

EXAMPLE X

The same procedure described in Example IX is repeated except the copolymer resin(Formula XII) (15 g) prepared according to Example VI is used to form an ultra-micro photoresist pattern(sensitivity: 14 mJ/cm$^2$).

EXAMPLE XI

The same procedure described in Example IX is repeated except the copolymer resin(Formula XIII) (15 g) prepared according to Example VII is used to form an ultra-micro photoresist pattern.

EXAMPLE XII

The same procedure described in Example IX is repeated except the copolymer resin (Formula XIV) (18 g) prepared according to Example VIII is used to form an ultra-micro photoresist pattern(resolution: 0.15 μm).

As described above, the copolymer resin according to the present invention is easily prepared by conventional radical polymerization due to the introduction of lithocholylacidyl (meth)acrylate monomer to the polymer structure. The copolymer resin has high transparency at 193 nm, and provides increased etching resistance. In addition, the copolymer resin in accordance with the present invention overcomes the prior art problem of crystal extraction, which occurs with the three component photoresist system when excessive dissolution inhibitors are used and free transition temperature (Tg) is lowered. Thus, the copolymer resin of the present invention is suitable for use with KrF or ArF light sources and can be usefully employed in lithography processes.

Many modifications and variations of the present invention are possible in light of the above teachings. Therefore, it is to be understood that within the scope of the appended claims, the invention may be practiced otherwise than as specifically described.

What is claimed is:

1. A copolymer comprising repeating units derived from:

(i) at least one monomer represented by the following formula:

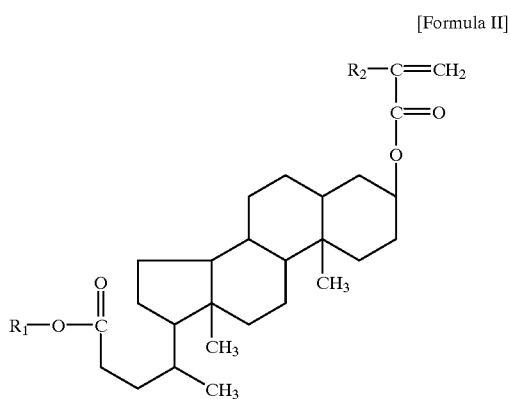

[Formula II]

wherein $R_1$ represents hydrogen, a substituted or non-substituted $C_1$–$C_{10}$ straight or branched chain alkyl group, a cycloalkyl group, an alkoxyalkyl group, or a cycloalkoxyalkyl group, and $R_2$ represents hydrogen or a methyl group;

and;

(ii) a monomer of the following formula:

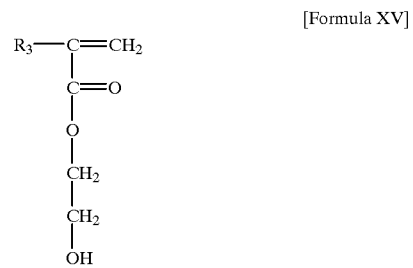

[Formula XV]

wherein $R_3$ is hydrogen or methyl.

2. A copolymer according to claim 1 represented by the following formula:

[Formula IX]

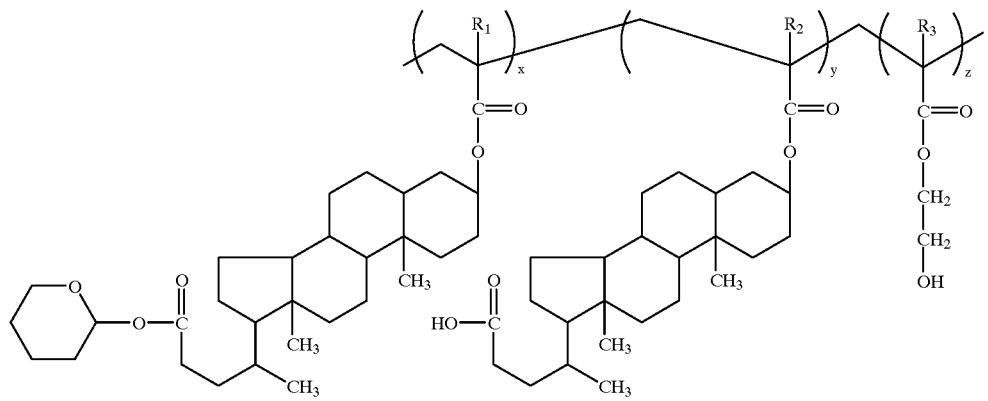

wherein, $R_1$, $R_2$ and $R_3$ independently represent hydrogen or a methyl group, x represents mole fraction between 0.005 to 0.9, and y and z independently represent a mole fraction between 0.001 and 0.9; or the following formula:

[Formula X]

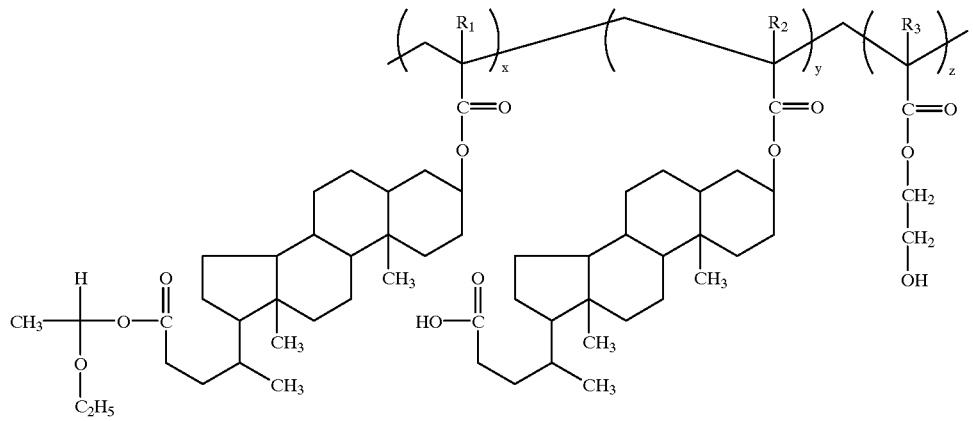

wherein, $R_1$, $R_2$ and $R_3$ independently represent hydrogen or a methyl group, x represents mole fraction between 0.005 to 0.9, and y and z independently represent a mole fraction between 0.001 and 0.9.

3. A copolymer according to claim 2 comprising poly[5-(hydropyranyl)-cholan-24-yl-3-(meth)acrylate/5-cholan-24-oic-acidyl-3-(meth)acrylate/2-hydroxyethyl(meth)acrylate] or poly[5-(2-ethoxyethyl) cholan-24-yl-3-(meth)acrylate/5-cholan-24-oic-acidyl-3-(meth)acrylate/2-hydroxyethyl (meth)acrylate].

4. A process for preparing a copolymer according to claim 1 comprising:

dissolving in a organic solvent, (i) at least one monomer represented by the following formula:

[Formula II]

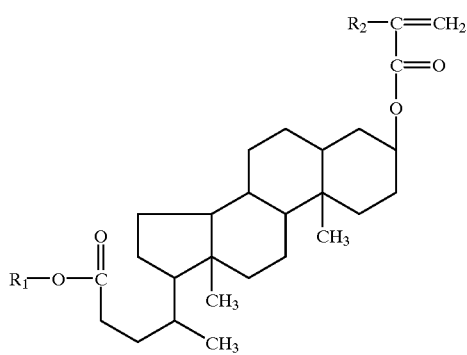

wherein $R_1$ represents hydrogen, a substituted or non-substituted $C_1$–$C_{10}$ straight or branched chain alkyl group, a cycloalkyl group, an alkoxyalkyl group, or a cycloalkoxyalkyl group, and $R_2$ represents hydrogen or a methyl group;

and;

(ii) a monomer of the following formula:

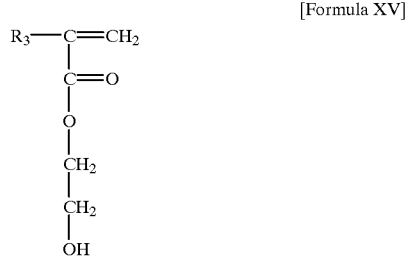

[Formula XV]

wherein $R_3$ is hydrogen or methyl; and polymerizing said monomer by adding a polymerization initiator to the resultant solution.

5. A process according to claim 4 wherein the organic solvent is cyclohexanone, methyl ethyl ketone, benzene, toluene, dioxane, or dimethylformamide.

6. A process according to claim 4 wherein the polymerization initiator is benzoyl peroxide, 2.2'-azobisisobutyronitrile, acetyl peroxide, lauryl peroxide, t-butyl peracetate, or di-t-butyl peroxide.

7. A photoresist composition comprising a copolymer of claim 1, an organic solvent and an inorganic acid generator.

8. A photoresist composition in accordance with claim 7 wherein the organic solvent is a compound selected from the group consisting of methyl 3-methoxypriopionate, ethyl 3-ethoxypropionate, propylene glycol methyl ether acetate, and cyclohexanone, and mixtures thereof.

9. A photresist composition in accordance with claim 7, wherein the inorganic generator is a compound selected from the group consisting of diphenyliodine hexafluoro phosphate, diphenyliodine hexafluoro arsenate, diphenyliodine, hexafluoro antimonate, diphenyl p-methoxyphenyl triflate, diphenyl p-tolulenyl triflate, triphenylsulfonium hexafluoro phosphate, triphenylsulfonium hexfluoro arsenate, triphenylsulfonium hexafluoro antimonate, triphenylsulfonium triflate, dibutylnaphthyl sulfonium triflate, and mixtures thereof.

10. A process for forming a photoresist pattern comprising the steps of:

(a) coating the photoresist composition of claim 7 on a wafer surface;

(b) exposing the wafer to a patterned light source;

(c) developing the resultant exposed wafer with developer to obtain a pattern.

11. A process for forming a photoresist pattern in accordance with claim 10, which further comprises the step of baking the wafer before or after the exposing step (b).

12. A process for forming a photoresist pattern in accordance with claim 11, wherein the baking step is carried out at a temperature between 70° C. and 200° C.

13. A process for forming a photoresist pattern in accordance with claim 10, wherein the exposing step is carried out using an ArF, KrF, E-beam, X-ray, EUV, DUV or ion-beam light source.

14. A semiconductor element comprising a substrate with a layer of the photoresist composition of claim 7 coated thereon.

* * * * *